United States Patent [19]

Sve et al.

[11] Patent Number: 4,550,255

[45] Date of Patent: Oct. 29, 1985

[54] VOID DETECTION AND COMPOSITION MEASUREMENTS IN COMPOSITE WIRES

[75] Inventors: Charles Sve, Palos Verdes Estates; Eric P. Muntz, Pasadena, both of Calif.

[73] Assignee: The United States of America as represented by the Secretary of the Air Force, Washington, D.C.

[21] Appl. No.: 511,060

[22] Filed: Jul. 5, 1983

[51] Int. Cl.$^4$ ............................................. G01N 23/18
[52] U.S. Cl. .................................... 250/359.1; 378/58; 378/156
[58] Field of Search .................... 378/58, 51, 59, 156; 250/358.1, 359.1, 360.1, 390–392

[56] References Cited

U.S. PATENT DOCUMENTS

| | | | |
|---|---|---|---|
| 2,584,583 | 2/1952 | Hillery, Jr. | 356/382 |
| 3,372,276 | 3/1968 | Reynolds et al. | 250/358.1 |
| 3,518,697 | 6/1967 | Martens | 346/33 |
| 3,715,588 | 2/1973 | Rose | 250/360.1 |
| 3,973,126 | 8/1976 | Redington et al. | 378/156 |
| 3,995,164 | 11/1976 | Ramsay et al. | 378/156 |
| 4,060,727 | 11/1977 | Verdickt | 250/358.1 |
| 4,161,656 | 7/1979 | Marcuse et al. | 250/459.1 |
| 4,292,522 | 9/1981 | Okumoto | 250/358.1 |

FOREIGN PATENT DOCUMENTS 1150193 4/1969 United Kingdom ................. 378/58

*Primary Examiner*—Alfred E. Smith
*Assistant Examiner*—Carolyn E. Fields
*Attorney, Agent, or Firm*—Donald J. Singer; Bobby D. Scearce

[57] ABSTRACT

A novel method and system for the detection of voids or other composition anomalies in wires and particularly in composite wires is provided, which comprises a source of penetrating radiation, such as an X-ray, gamma or neutron source for irradiating the wire; a fluid bath in which the wire is immersed or through which the wire may be moved, the bath containing a material having a linear coefficient of attenuation for the radiation closely matching that of a standard or ideal composition wire; and a detector system for observing and comparing the transmission of the radiation through the bath and wire with that through the bath only, or through the bath and wire with that through the bath containing a normal or standard wire.

16 Claims, 8 Drawing Figures

VOID DETECTION AND COMPOSITION MEASUREMENTS IN COMPOSITE WIRES

RIGHTS OF THE GOVERNMENT

The invention described herein may be manufactured and used by or for the Government of the United States for all governmental purposes without the payment of any royalty.

BACKGROUND OF THE INVENTION

The present invention relates generally to methods and apparatus for nondestructive radiographic examination of materials, and more particularly to a novel method and apparatus for the nondestructive inspection of composite wire.

Nondestructive testing procedures for routine examination of composite wire structural integrity, as, for example, in a production setting, have not been developed. Testing of composite wires is particularly difficult because existing manufacturing processes produce composite wire which may vary substantially in cross-sectional geometry and size, surface properties, and matrix/fiber composition. Because the intended use of the wire may frequently be as starting material in the fabrication of diffusion bonded composite structures comprising fabric or layers of the composite wire, wide variations in wire geometry, surface finish and composition may be tolerable without substantially affecting the quality of the fabricated composite structure. Nevertheless, because as-manufactured composite wire may be as just characterized, the nondestructive examination of finished wire for the existence of voids which significantly affect wire strength is extremely difficult using conventional methods. For example, nondestructive testing techniques based on observation of wire resistance, surface emissivity, ultrasonics, infrared imaging, and other familiar methods are often difficult to intercept because of these tolerated characteristics. Further, these familiar techniques are severely limited in their utility for examining wire quickly, in large quantity, or automatically. Wire imaging using radiographic techniques is also difficult because large lengths of wire must be examined with a resolution in the plane of the wire exceeding 50 line pairs per millimeter, which is difficult using detection techniques other than X-ray filming. The use of X-ray film for examining large quantities of wire, however, is not practical and would require a sophisticated image scanning densitometer, and the processing of huge amounts of data using some flaw detection algorithm.

The present invention eliminates or substantially reduces in critical importance the above described problems and inadequacies in existing nondestructive wire testing technology by providing a novel system and technique for examination of composite wire for the detection of voids or other composition anomalies. In the practice of the invention, a test wire is irradiated with penetrating radiation as the test wire is immersed in or drawn through a fluid bath having an attenuation coefficient for the radiation matching that of the material comprising a normal or standard wire. A pair of detectors adjacent the bath monitor the transmission of the radiation along separate paths through the bath and test wire and through the bath only, and compare the two transmissions to provide a measure of any voids extant in the test wire. Alternatively, the transmission through the bath and test wire may be compared to that through the bath and a standard or normal composition wire. Voids in the test wire are detected as severe composition anomalies. The fluid bath automatically adjusts to changes in wire size and geometry. Therefore, the technique of the present invention is independent of variations in test wire size or geometry, as might characterize as-manufactured composite wire, and readily identifies voids in the wire by observing changes in the average composition of the test wire. Though the specific embodiment disclosed utilizes X-ray, it is understood that other penetrating radiation, such as gamma or neutron radiation, used in conjunction with a fluid bath exhibiting appropriate attenuation characteristics may also be used within the scope of these teachings. The relative signal levels obtainable in detecting composition variations using this technique allow observation of void fractions in the composite wire of as low as about one percent.

It is, therefore, an object of the present invention to provide an improved nondestructive testing system and method.

It is a further object of the invention to provide a novel method for the nondestructive examination of wire.

It is yet a further object of the invention to provide an efficient and accurate system for the nondestructive testing of composite wire using penetrating radiation.

These and other objects of the present invention will become apparent as the detailed description of specific representative embodiments thereof proceeds.

SUMMARY OF THE INVENTION

In accordance with the foregoing principles and objects of the present invention, a novel method and system for the detection of voids or other composition anomalies in wires and particularly in composite wires is provided, which comprises a source of penetrating radiation, such as an X-ray, gamma or neutron source for irradiating the wire; a fluid bath in which the wire is immersed or through which the wire may be moved, the bath containing a material having a linear coefficient of attenuation for the radiation closely matching that of a standard or ideal composition wire; and a detector system for observing and comparing the transmissions of the radiation through the bath and wire with that through the bath only, or through the bath and wire with that through the bath containing a normal or standard wire.

DESCRIPTION OF THE DRAWINGS

The present invention will be more clearly understood from the following detailed description of specific representative embodiments thereof read in conjunction with the accompanying drawings wherein.

DETAILED DESCRIPTION

Figure 1:
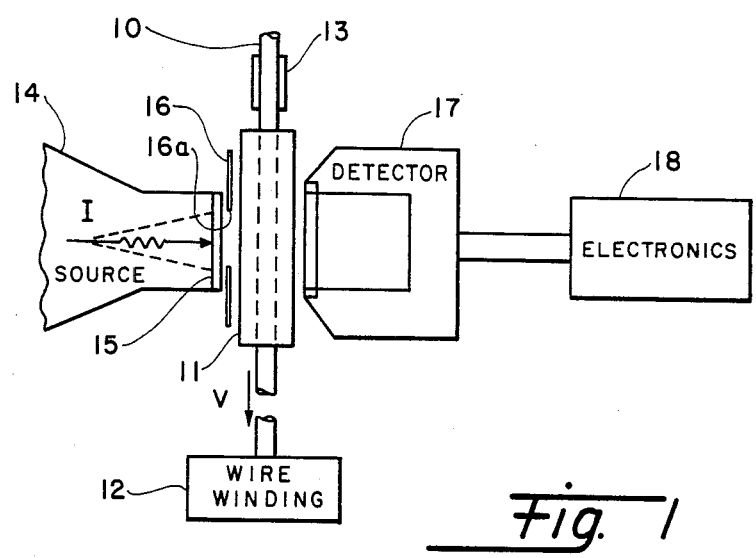
FIG. 1 is a schematic plan view of one representative embodiment of the present invention.

Referring now to FIG. 1, presented therein is a schematic plan view of the essential elements of the present invention arranged in a representative configuration illustrating the system and method for testing of wires. A test wire 10 to be examine is immersed in or drawn through a fluid bath 11. As will be apparent from these teachings the system and method described herein may be applicable both to static tests wherein the wire is merely stationary within fluid bath 11, or to tests wherein test wire 10 is moved through bath 11 at a predetermined speed v. Therefore, a winding means 12 or the like may be included to pass test wire 10 through bath 11 at a predetermined speed v. A lead-in device and positioning means 13, in the form of rollers, channels, tubes and the like, is included, which, in cooperation with means 12, guides wire 10 through bath 11 in manner and location suitable for inspection according to the present invention. As hereinafter discussed in more detail, lead-in means 13 should position wire 10 within bath 11 to an accuracy of about ±0.1 wire diameters.

Fluid bath 11 contains a material exhibiting a linear attenuation coefficient $\mu$ (E) for the radiation being used which closely matches that of a nominally ideal or standard wire averaged over its cross section. In the examination of composite wires, the fluid bath 11 is normally selected as having an attenuation coefficient matching the average absorption coefficient of the composite. However, for the examination of wires for certain defects, for example in wires manufactured with a substantially constant amount of reinforcement fibers, where it is important to detect voids in the matrix, it may be desirable to select a bath 11 material having a coefficient closely matching that of the matrix material rather than that of the average composition. Bath 11 is configured to provide simultaneously a first path for radiation transmission through the bath 11 material only and a second path through the bath and a test wire 10, or, alternatively, as discussed below in relation to FIG. 5, a first path through bath 11 and a standard wire and a second path through the bath and a test wire 10.

Figure 2A:
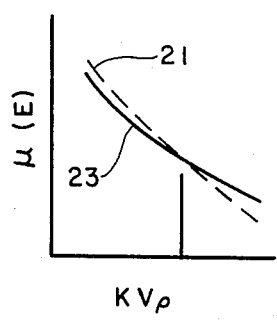
FIGS. 2a and 2b illustrate diagrammatically a relationship between the linear absorption coefficient of the bath and an ideal or standard wire material.
Figure 2B:
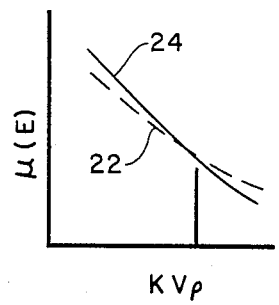

The fluid contained in bath 11 preferably comprises a high atomic number element dissolved in a solvent. In many cases the high atomic number element will be bound within a soluble complex. The bath must be such as to not chemically attack the composite wire and in particular not to produce small gas bubbles which would generate spurious flaw signals. Examples of useable bath fluids include the radiographic barium or iodine containing contrast agents used in diagnostic radiographic procedures. In the present application, there is an advantage to arranging for the effective linear absorption coefficient of the bath 11 to have a slightly different slope as plotted against photon energy than that characteristic of a standard, or ideal wire. FIGS. 2a and 2b illustrate representative plots of attainable effective linear absorption coefficient $\mu(E)$ versus photon energy $kV_p$ for a bath 11 material (dotted graphs 21 and 22) compared to a standard composition wire (solid graphs 23 and 24). The curves for bath 11 in each case represented in FIGS. 2a and 2b preferably have slightly different slopes than that of the standard wire so that there exists a characteristic value for $kV_p$ at which $\mu(E)$ for the bath 11 equals that of the standard wire. Bath 11 may then be matched to the standard wire for $\mu(E)$ by suitable selection or adjustment of $kV_p$, which is relatively easy to do, rather than by adjustment of the solute concentration of bath 11, which may be difficult to do to the required accuracy if the curves for bath and standard wire have substantially the same shape.

The bath 11 material will ordinarily require temperature control means (not shown) to maintain bath temperature within an optimum operating range. Concurrently, the temperature of the entering wire 10 will preferably be maintained at a temperature consistent with the desired bath 11 operating temperature. Further, the bath 11 material should be circulated and filtered routinely to remove particulate contaminants which may adversely affect the radiation transmission characteristics of bath 11. Therefore, it may be highly desirable to preclean wire 10 to remove surface particles, burrs and other contaminants prior to immersion into bath 11.

The bath 11 will preferably have a thickness (i.e., dimension perpendicular to wire 10 and parallel to the direction of radiation propagation (I) which is from about 1.25 to about 2.0 wire 10 diameters. Maintaining this dimension (bath 11 depth) at a practical minimum optimizes sensitivity of the detection method herein described by avoiding unnecessary absorption of the penetrating radiation within bath 11.

A source 14 of penetrating radiation I is disposed adjacent fluid bath 11 so that wire 10 and bath 11 are illuminated with radiation passing through radiation window 15. Radiation source 14 may comprise any suitable source of penetrating radiation, such as X-ray, gamma, or neutron as might be available from an electron beam source, a radioactive source, or radiation generator. In the work done in demonstration of the invention herein, a commercially available X-ray source comprising an electron beam source and a tungsten anode was used in conjunction with a window 15 of beryllium. An X-ray opaque screen 16 having aperture 16a may be positioned between source 14 and bath 11 as shown in FIG. 1 to suitably collimate the beam to a size no larger than that required to illuminate the detector 17 as hereinafter described. The sample composite wire examined comprised a composite of graphite fiber in an aluminum matrix, and, accordingly, a bath containing iodine in solution was chosen as having the same linear attenuation coefficient as that of the nominal standard wire composition.

A detector system 17 is disposed adjacent bath 11 and opposite radiation source 14 to measure the transmission Of radiation I through bath 11 or through bath 11 and a standard wire, and, separately, the transmission through both bath 11 and test wire 10, along equal transmission path lengths, and to provide separate outputs characteristic thereof. Accordingly, suitable electronics 18 were included to compare the signals generated by the detector system 17 and to display the results of the comparison. If test wire 10 has the standard or nominal composition, i.e., if no voids or other composition anomalies are present, both signals will be the same. Deviations from the nominal wire 10 composition are manifested by differences in the two signal levels.

In the examination of wires for existence of, for example, voids at a desirably low void fraction level, the detector system 17 selected for use must provide good stability and low noise injection, and, because the anomalies to be detected are small, only errors of about one part in 10,000 may be tolerated. Therefore, high pressure ionization chambers may be the most desirable for use in the present invention because of their characteristic stability and low noise injection. However, because of the requirement herein of a certain degree of imaging or resolution capability of the detector system 17 to differentiate the signal representative of the radiation transmission through the bath 11 from that through the bath 11 and wire 10 sample, a high pressure imaging ionization chamber having a segmented sensing electrode was selected for use in one demonstration of the invention herein. It is understood, however, that detector selection is not limiting of the invention herein, as other detector system types, such as sodium iodide or other scintillators, solid state radiation detectors, and the like, may also be suitable for use, depending on the radiation source selected for use, within the intended scope of these teachings.

Figure 3:
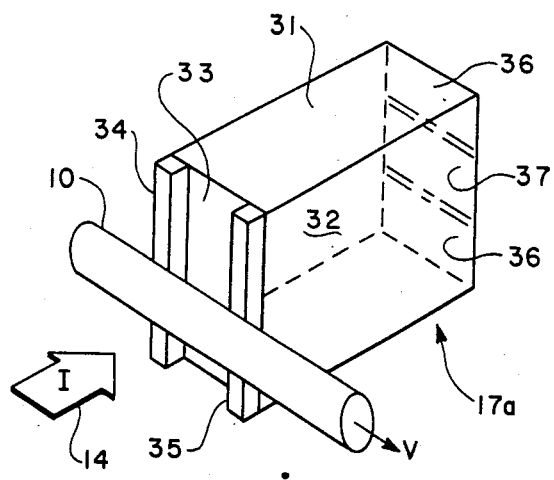
FIG. 3 is an isometric drawing of a detector system useful in the practice of the invention.

FIG. 3 shows one representative ionization chamber detector system 17a suitable for use. Detector system 17a comprises a high pressure ionization chamber 31 defining a detector volume 32 filled with an imaging gas at high pressure. In demonstration of the invention, wherein an X-ray source was used, krypton at about 10 atmospheres was used as the imaging gas, although other gases such as Freon 13B1 (containing bromine) or xenon, or suitable liquids such as tetramethyl tin may also be useable. Ionization chamber 31 includes a pressure window 33 near wire 10 and confronting the source 14 of X-rays I, as suggested in FIG. 3 for admitting into detector volume 32 the X-rays transmitted by wire 10 and bath. (The fluid bath is not shown in FIG. 3 for clarity of illustration.) The pressure window 33 is defined between adjustable stops 34 and 35 and defines the length of wire 10 which is momentaneously examined as the wire 10 is moved through the bath past the detector system. Window 33 of detector 17a may desirably be placed so that it receives radiation from an area corresponding to the complete cross section of wire 10 and a substantially equal width of the bath above and below wire 10. The length of wire 10 between stops 34, 35 selected for momentaneous examination is arbitrary but may conveniently be selected as about 0.5 to about 10 mm.

Pressure window 33 serves as the cathode of the ionization chamber detector 17a as shown in FIG. 3, and is typically held at a potential of about −20 to about −25 kV. Opposite pressure window 33 is a segmented electrode configuration comprising a pair of outer electrodes 36 for monitoring X-ray transmission through the bath 11 only, and an inner electrode 37 for monitoring X-ray transmission through bath 11 and wire 10. Typically the electrodes 36, 37 comprise the anode(s) of the ionization chamber 31 and are held substantially at ground potential. The electrodes typically comprised vapor deposited gold films approximately 1 mm wide by about 15 mm long, with a gap of about 3 mm maintained between adjacent electrodes sufficient to preclude current leakage therebetween. In making the electrical connections to the respective electrodes 36, 37 to interconnect detector 17a to the associated electronics 18 (as suggested in FIG. 1), care must be taken to properly insulate the electrode leads so that well defined areas of the electrodes 36, 37 remain active.

The depth of the gas in the ionization chamber 31 (i.e., interelectrode spacing between window 33 and electrodes 36, 37) required along the X-ray beam propagation direction, for substantial absorption, is dictated by the pressure within detector volume 32 (conveniently about 10 atm) and the X-ray beam average energy. Typically, a 1 to 2 cm interelectrode spacing at the stated pressure will provide substantially complete absorption of X-ray photons below about 25 keV. In the operation of the detector 17a, X-ray photons from source 14 traversing bath 11 and wire 10 through pressure window 33 are absorbed in the imaging gas within detector volume 32, and the electrons that are produced as a result of the absorption events have a short range in the high pressure gas. A relatively large number of electron-ion pairs are produced, and the electric field maintained between pressure window 33 and segmented electrodes 36, 37 is sufficient to cause the electrons generated within volume 32 to migrate to the particular electrode 36 or 37 characteristic of the zone within volume 32 at which the electrons are generated. Very little cross diffusion of electrons takes place from a zone within volume 32 affected by X-ray transmission through bath 11 only (e.g., upper and lower regions of volume 32) to the zone affected by X-ray transmission through bath 11 and wire 10 (middle region of volume 32), if the electric field between window 33 and segmented electrode system 36, 37 is maintained at a level greater than about 1500 volts/mm. Therefore, the X-ray intensity distribution within volume 32 is reflected in the charge density distribution at the respective electrodes 36 or 37. For the purpose of the present invention, it is highly desirable to have a well defined wire 10 image area; therefore, the inner electrode 37 of segmented electrode system 36, 37 shown in FIG. 3 will typically be of area corresponding to the diameter of wire 10 as imaged (magnified) across the length of the ionization chamber 31 from X-ray source 14 to segmented electrodes 36, 37. Providing an inner electrode 37 having an area with a dimension perpendicular to the test wire 10 significantly greater than the magnified wire diameter's image will ordinarily substantially reduce the ability of detector system 17a to differentiate the signals produced by the inner 37 and outer 36 electrodes of the segmented electrode system.

Figure 4:
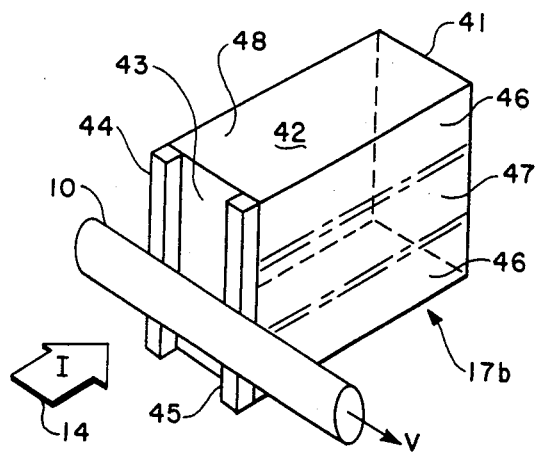
FIG. 4 is an isometric drawing of an alternative detector system.

Detector system 17 may preferably be configured as suggested in FIG. 4 as detector system 17b. The configuration as set forth in FIG. 4 comprises a structure for detector system 17b wherein the electrodes between which detector volume 42 is defined are disposed at confronting lateral surfaces of ionization chamber 41. Adjustable stops 44, 45 serve the same purpose as correspondingly named elements of the FIG. 3 configuration. Between stops 44, 45 is defined pressure window 43 for admission of X-rays I from source 14 into detector volume 42. Cathode 48 comprises one side of chamber 41 and segmented electrode system 46, 47 are on the opposite side, substantially as shown. Outer electrodes 46 and inner electrode 47 are configured similar to the respective electrodes 36, 37 of the FIG. 3 configuration and function in equivalent fashion. In the FIG. 4 configuration, however, detector system 17b may be sized approximately the same as detector 17a of FIG. 3, but the interelectrode spacing (between cathode 48 and segmented electrodes 46, 47) is substantially less than that which characterizes detector 17a. The interelectrode spacing of detector 17b is typically about 3 mm, and, therefore, the cathode 48 may typically be maintained at a substantially lower potential (e.g., about −4000 to −5000 volts). The detector system 17b produces the same information as the detector system 17a of the FIG. 3 configuration provided the area of inner electrode 47 corresponds substantially to the wire 10 image area. Because the higher operating voltage characteristic of the FIG. 3 configuration was more conducive to noise injection resulting from current leakage between electrodes 36, 37 of the segmented electrode system thereof, the FIG. 4 configuration was selected for work performed in demonstration of the utility and operability of the invention as hereinbelow described. The current leakage between electrodes 46, 47 of detector 17b was observed to be less than about $10^{-12}$ amp.

Figure 5:
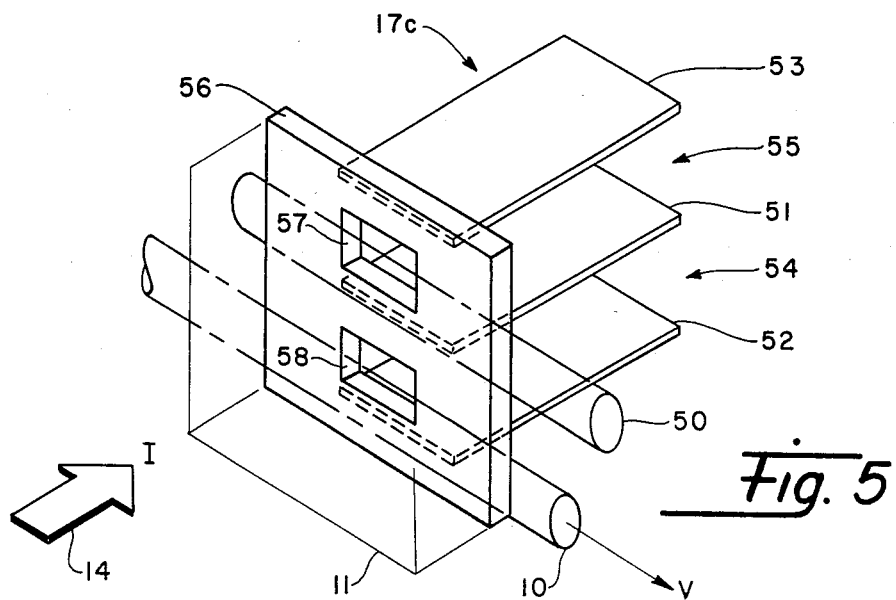
FIG. 5 is a schematic of another detector configuration especially useful in comparing immersed test wire with a standard or ideal wire.

A further representative detector 17c configuration useful in the practice of the present invention may be that depicted schematically in FIG. 5. In this configuration, the high voltage electrode, cathode 51, is disposed intermediate the two current measuring electrodes, anodes 52 and 53. For simplicity of illustration in FIG. 5, the housing for detector system 17c which defines the detector volumes analogous to that for detector systems 17a and 17b described previously is not shown. Two detector volumes 54 and 55 are therefore defined, respectively, between cathode 51 and anode 52, and between cathode 51 and anode 53. A standard or normal wire 50 of nominal composition may be disposed within bath 11 and is imaged by X-ray source 14 onto monitor detector volume 55 to provide a reference for examination of test wire 10. Test wire 10 is immersed in or drawn through bath 11 as described previously with respect to FIGS. 1, 3, and 4, and is imaged onto signal detector volume 54. The imaging of standard wire 50 and test wire 10 onto their respective detector volumes is controlled by a spatial filter defined by X-ray opaque screen 56 (comprising such as lead) having entrance apertures 57 and 58, respectively, to monitor detector 55 and signal detector 54. Detector system 17c provides an advantage over those described above in that it does not have to provide imaging and can be operated at a lower potential difference ($\sim -500$ v to $\sim -150$ v) thus exhibiting a lower leakage current than that characterizing the FIG. 3 or 4 configurations.

The configuration utilizing a spatial filter (FIG. 5) may, optionally, include an alternative detector type, such as a pair of solid state scintillators or liquid ionization chambers, although the embodiment of FIG. 5 may be preferred. The alternative use of a standard wire 50 in the monitor (reference) channel, as shown in FIG. 5, may be advantageous in cancelling out the effects of small variations in bath 11 absorption coefficient. Standard wire 50 may be permanently mounted in the monitor channel (in front of reference detector 55) or periodically moved into and out of the channel using appropriate means.

In all detector configurations herein described, any wire image (test or standard) is sampled from an area defined by a distance in a direction perpendicular to both the wire length and beam I propagation direction, which, at the position of the wire is equivalent to the largest diameter ($D_{max}$) that the test wire might exhibit within the manufacturing tolerances, but no greater than about 1.25 $D_{max}$ since the sensitivity of the technique to wire flaws decreases with increase of that amount of radiation transmission observed by the signal detector as passing through bath 11 material only. A preferred sampling width $W_s$ (height of aperture 58) may then be defined as $D_{max} < W_s < 1.25\ D_{max}$. The actual observed (by the detector) width would be somewhat larger due to the image magnification of the wire within the detector volume.

The degree of absorption of the wire and detectability of voids therein may be demonstrated by a simple analytical example. Assume a standard wire is a composite of aluminum and graphite, having a volume percent of graphite represented by $X_c$. Then the aluminum volume percentage $X_{Al}$ is given by $X_{Al}=1-X_c$. For an average density of the composite comprising the wire of 2.42 gm/cc, $X_{Al}$ is equal to 0.6 and $X_c=0.4$. If $\mu_{Al}$ and $\mu_c$ are the linear attenuation coefficients for aluminum and graphite, respectively, then the attenuation of an X-ray beam may be represented by $$\frac{I}{I_o} = \exp - (0.4\mu_c d + 0.6\mu_{Al} d) = \exp(-\mu_{eff} d)$$

where $I_o$ is the intensity of the X-ray source, I is the intensity of the transmission through the wire and d is the distance through the wire in the direction of beam propagation. For a convenient source of X-ray, such as 10 mCi of iodine-125 (mostly 27.3 keV) the attenuation over the nominal diameter of a 0.025 in (0.635 mm) wire is 0.845, and a total number of photons seen by the detector over a 1 diameter length of wire is about $1.15 \times 10^5$/sec. A 0.001-in void in the wire would result in a 0.69% change in the count rate, which corresponds to an observed ion chamber current of about $10^{-11}$ amp.

Experimental determinations were made on selected wires of graphite fiber-aluminum composite to demonstrate the utility and operation of the apparatus and method of the present invention in detecting voids within the wire. The commercially available electron beam generated X-ray source described above was used as source 14. The detector system 17 configuration was that as suggested in FIG. 4 initially, and in subsequent tests, the configuration of FIG. 5 was used. The bath 11 comprised commercial contrast agents Renographin TM 60 and 76, containing, respectively, 0.290 and 0.370 gm/cc of iodine. Measurements of the effective attenuation coefficients of the 0.290 and 0.370 gm/cc iodine concentration baths and on a 1.25 mm sheet of aluminum showed that the best match of coefficients for the bath and aluminum was the 0.290 cm/cc bath at about 22 keV and the 0.370 gm/cc bath at about 18.5 kV$_p$ (where kV$_p$ is the setting on the X-ray generator control and represents the keV of the electron beam). Substantial match of the coefficients for both baths were good throughout the 25–30 keV range.

Figure 7:
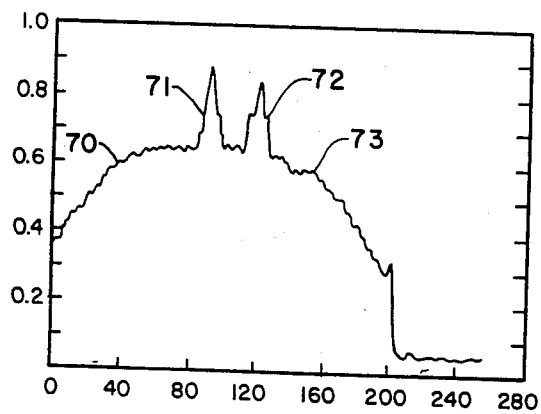
FIG. 7 is a densitometer trace of a representative normal wire and two flawed wires as viewed through a representative bath material.
Figure 6:
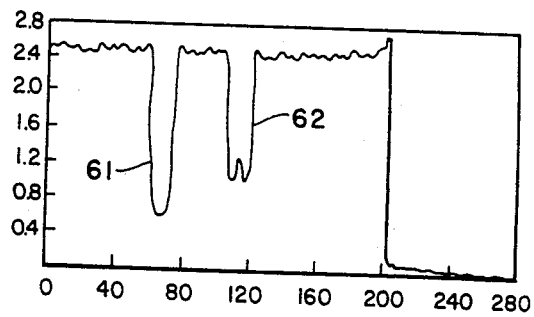
FIG. 6 is a densitometer trace of an X-ray image of a representative normal composite wire and of a flawed wire.

X-ray film radiographs were taken of an aluminum wire, a composite wire of good quality, and a composite wire containing voids. Microdensitometer traces of the film along an arbitrarily selected path perpendicular to the wires are shown in FIGS. 6 and 7. FIG. 6 presents the densitometer trace of the radiograph of a quality wire as shown at trace 61 and a flawed wire at trace 62, with no bath surrounding the wires. The detectability of the flaw in the wire represented by trace 62 is apparent. FIG. 7 presents traces of two flawed wires and one quality wire as viewed through a bath that balances the good wire. Again, the presence of flaws in the wires represented by traces 71 and 72 is apparent, whereas the quality wire at trace 73 demonstrates substantial identity with the baseline trace 70 representing the bath transmission only. The curvature of the baseline trace 70 of the bath results from changes in bath depth due to surface tension.

The present invention, as herein described in a representative embodiment thereof, therefore provides a novel method and apparatus for the detection of voids or other composition anomalies in materials, and particularly composite wires. Using commercially available X-ray sources with stationary, uncooled anodes, void fractions of less than about 3% may be detectable at wire speeds of about 10 cm/sec. The resolution along the wire length would be from about 1 mm, as suggested by the information gathered on the graphite fiber-aluminum matrix wires tested in demonstration of the invention. Judicious selection of the X-ray source, fluid bath, and detector may allow substantially higher wire speeds with acceptable wire resolution and statistical accuracy of the detector output.

It is understood that the invention may be applicable to the examination of materials and sample shapes other than that specifically described in the representative examples given, and the substitution of alternative bath materials and compositions, radiation sources, detector means and configuration, and other elements comprising the claimed invention may be made, as would occur to one with skill in the field of this invention, within the intended scope of these teachings. Therefore, all embodiments contemplated hereunder have not been shown in complete detail. Other embodiments may be developed without departing from the spirit of this invention or from the scope of the appended claims.

We claim:

1. Apparatus for the nondestructive inspection of wire, comprising:
   a. a source of penetrating radiation;
   b. a fluid bath for immersing said wire disposed adjacent said source, said bath comprising a material having a coefficient of attenuation of said penetrating radiation substantially equal to that of the material of said wire, said bath further configured to provide first and second paths for said penetrating radiation defined through said bath, said second path defined through said wire and surrounding bath material, said first and second paths having substantially identical path lengths; and
   c. a detector means for separately detecting the intensities of penetrating radiation transmitted, respectively, along said first and second paths, and for providing respective output signals porportional thereto.

2. The apparatus as claimed in claim 1 further comprising means for comparing said output signals.

3. The apparatus as recited in claim 1 further comprising a wire segment, said segment conforming in preselected size and composition to that characterizing a standard for said wire and disposed in said bath along said first path.

4. The apparatus as claimed in claim 1 wherein said source of penetrating radiation comprises an X-ray source.

5. The apparatus as recited in claim 1 wherein said detecting means comprises an ionization chamber.

6. The apparatus as claimed in claim 1 wherein said source of penetrating radiation comprises a neutron source.

7. The apparatus as recited in claim 1 wherein said source of penetrating radiation comprises a gamma source.

8. The apparatus as recited in claim 1 further comprising means to move said wire through said bath at a predetermined rate.

9. The apparatus as recited in claim 1 wherein said fluid bath material comprises iodine.

10. A method for nondestructively inspecting wire, comprising the steps of:
    a. providing a source of penetrating radiation;
    b. immersing said wire in a fluid bath comprising a material having an attenuation coefficient for said penetrating radiation substantially equal to that of the material of said wire;
    c. irradiating said bath and wire with said penetrating radiation along first and second paths defined through said bath, said second path defined through said bath and wire;
    d. detecting separately the intensities of radiation transmitted along said paths; and
    e. comparing said intensities.

11. The method of claim 10 wherein step c is characterized by further providing a wire segment, conforming in preselected size and composition to that characterizing a standard for said wire, within said bath along said first path.

12. The method as recited in claim 10 further comprising, following step b thereof the step of moving said wire through said bath at a predetermined rate.

13. The method as recited in claim 10 wherein said source of penetrating radiation comprises an X-ray source.

14. The method as recited in claim 10 wherein said source of penetrating radiation comprises a gamma source.

15. The method as recited in claim 10 wherein said source of penetrating radiation comprises a neutron source.

16. The method as recited in claim 10 wherein said bath material comprises iodine.

* * * * *